United States Patent
Cox et al.

(10) Patent No.: US 6,926,710 B2
(45) Date of Patent: Aug. 9, 2005

(54) METHOD AND SYSTEM FOR IMPROVING VISION

(75) Inventors: Ian G. Cox, Honeoye Falls, NY (US); Timothy N. Turner, West Jordan, UT (US); Gerhard Youssefi, Landshut (DE)

(73) Assignee: Bausch and Lomb Incorporated, Rochester, NY (US)

(*) Notice: Subject to any disclaimer, the term of this patent is extended or adjusted under 35 U.S.C. 154(b) by 58 days.

(21) Appl. No.: 10/045,694

(22) Filed: Oct. 19, 2001

(65) Prior Publication Data

US 2002/0082629 A1 Jun. 27, 2002

Related U.S. Application Data

(60) Provisional application No. 60/241,869, filed on Oct. 20, 2000.

(51) Int. Cl.[7] .............................................. A61B 18/18
(52) U.S. Cl. ............................. 606/5; 606/10; 128/898
(58) Field of Search ............................. 606/4–6, 10–12; 128/898; 351/208–212

(56) References Cited

U.S. PATENT DOCUMENTS

| | | | | |
|---|---|---|---|---|
| 5,098,426 A | | 3/1992 | Sklar ............................... 606/5 |
| 5,777,719 A | * | 7/1998 | Williams et al. ............ 351/212 |
| 5,782,822 A | * | 7/1998 | Telfair et al. .................. 606/5 |
| 6,090,100 A | * | 7/2000 | Hohla .............................. 606/5 |
| 6,099,522 A | * | 8/2000 | Knopp et al. ................. 606/10 |
| 6,129,722 A | * | 10/2000 | Ruiz ............................... 606/5 |
| 6,413,251 B1 | * | 7/2002 | Williams ........................ 606/5 |

FOREIGN PATENT DOCUMENTS

| | | | |
|---|---|---|---|
| DE | 199 04 753 C1 | 9/2000 | ........... A61F/9/008 |
| EP | 0 770 370 A | 5/1997 | ............. A61F/9/00 |
| WO | 93 16631 A | 9/1993 | ............. A61B/5/02 |
| WO | 95/27534 | 10/1995 | ............. A61N/5/02 |
| WO | WO 00/45759 | 10/2000 | ........... A61F/9/008 |

* cited by examiner

Primary Examiner—A. Farah

(57) ABSTRACT

Methods and apparatus for improving vision incorporate the effects of biodynamical and biomechanical (biological) responses of the eye. The eye produces a biological response to trauma, such as a LASIK keratectomy or other necessary traumatic procedure in preparation for refractive surgery. By observing the biological response, a prospective treatment to correct higher order aberrations is adjusted to compensate for the biological effects. An improved photorefractive surgery system incorporates one or more suitable diagnostic devices that provide biological response information in such a manner that the patient need not change position from that assumed for the surgical procedure.

20 Claims, 3 Drawing Sheets

METHOD AND SYSTEM FOR IMPROVING VISION

This application claims the benefit of provisional application No. 60/241,869 filed Oct. 20, 2000.

BACKGROUND OF THE INVENTION

1. Field of the Invention

The invention relates generally to methods and apparatus for photorefractive correction of vision, and more particularly to the adjustment of higher order aberrations in consideration of biodynamical and biomechanical responses of the eye.

2. Description of Related Art

The field of photorefractive surgery for vision correction continues to grow rapidly. The number of procedures demanded by consumers is constantly increasing at the same time that researchers and practitioners are learning more about vision and how to correct it. The application of excimer laser technology including refinements in beam size, shape, and placement, active eye tracking, and diagnostic instrument development including topographers, wavefront sensors, ultrasound, and OCT's underscores the progress in this field.

What has become evident as understanding continues to unfold about what perfect vision really is, is that models need to be developed which describe the eye and its various responses to attempts at vision correction. The advent of wavefront sensing in ophthalmology is driving now traditional procedures such as photorefractive keratectomy (PRK) and LASIK which were primarily concerned with correcting refractive errors such as defocus and astigmatism (myopia, hyperopia, and astigmatic forms thereof), to the investigation and performance of more sophisticated procedures in which higher order optical aberrations (herein referred to as third and higher Zernike order or equivalent) are being addressed. These higher order monochromatic aberrations include, for example, spherical aberration, coma, and others as well understood by those skilled in the art.

The inventors of the present invention have recognized that directly eliminating all wavefront aberrations of the eye is not necessarily the key to emmetropia, because the act of photorefractive correction itself induces certain defects that must be accounted for in developing a photorefractive treatment. Accordingly, the invention is directed to methods and apparatus for developing and performing photorefractive treatments in view of these observations and which result in better objective and subjective visual evaluation.

SUMMARY OF THE INVENTION

Various embodiments of the invention are directed to methods and apparatus for improving vision by correcting higher order optical aberrations of the eye in consideration of biodynamic and biomechanic effects and responses of the eye.

In an embodiment of the invention, a method for developing a photorefractive treatment of a patient's eye involves making a diagnostic measurement to determine lower (second Zernike order or below) and/or higher (third and higher Zernike order) optical aberrations and adjusting a prospective photorefractive treatment based upon an expected, observed, calculated or otherwise anticipated biodynamical and/or biomechanical effect. Such an effect induces a deviation from an expected result of the prospective treatment in the absence of such biodynamical and/or biomechanical induced deviation. This adjustment will advantageously be a calculated or derived adjustment, however, empirical adjustments are entirely suitable as they form a basis for building and/or validating biodynamical and biomechanical models of the eye. Diagnostic measurements of the eye include directly measured or derived wavefront aberration measurements, topographic measurements including surface contours, eye component thicknesses, decentration, line of sight, height variation, etc., OCT measurements, ultrasound, and pachymetry measurements. The developed photorefractive treatment preferably includes photoablation by an excimer laser having appropriate beam sizes, shapes, and placements. Laser beam diameters at a target surface on the eye preferably range between 0.5 mm to 7 mm and may include different, multiple beam diameters within this range. In an aspect of this embodiment, further diagnostic measurements are made that are indicative of the shape of the stromal surface of the patient's eye which underlies the epithelium, for example, the stromal surface shape below a LASIK flap or non-uniform or otherwise abnormal thickness epithelial layer. Based upon empirical observations to date, it is preferable that the sum total of rotationally symmetric aberrations, e.g., spherical aberration, be equal to or greater in magnitude than the sum total of rotationally asymmetric aberrations, e.g., coma.

In another embodiment of the invention for correcting higher order aberrations of a patient's eye, a method comprises the steps of making any necessary physical intrusions upon the eye as, for example, keratectomy for a LASIK procedure, hereinafter referred to as trauma to the eye; obtaining diagnostic wavefront information at some time after the infliction of the trauma; and developing a photorefractive treatment for correcting the higher order aberrations of the patient's eye based at least in part upon the subsequent wavefront information. The wavefront information can be directly obtained by a wavefront measuring instrument or derived through indirect measurements based upon topography or other diagnostics as one skilled in the art will understand. In this exemplary embodiment, the LASIK cut is made but the flap is not lifted prior to making the diagnostic wavefront measurement. When the necessary trauma is inflicted upon the eye, the eyes biological response will show up as wavefront aberrations that are different from the wavefront aberrations of the eye prior to inflicting the trauma. In addition, the effect of the trauma as determined by corneal topographic measurements of corneal thickness and the anterior and especially posterior surfaces (where the effect is the largest), can be used to predict the total biomechanical response once the photo-ablative procedure is complete. Based upon an observed, derived, calculated or otherwise obtained indication of the biological response of the eye, a prospective treatment profile based upon an unconsidered biological response is modified to compensate for biological effects. The duration of time between inflicting the trauma and making the diagnostic measurement to obtain wavefront information will depend at least in part upon the severity, nature and extent of the biological effect in response to the trauma. It will therefore be appreciated by the practitioner what a suitable duration will be. In an aspect of this embodiment, a biomechanical effect can also be used to adjust the developed treatment. Non limiting examples of biodynamical effects include edema and epithelial growth, while a non-limiting example of a biomechanical effect is epithelial hole filling due to eyelid pressure. Biomechanical effects can be discerned from, for example, epithelial thickness measurements using high frequency ultrasound as described in the literature. It is again preferable based on empirical observation that the resultant sum total of the rotationally symmetric aberrations equal or exceed the sum total of the rotationally asymmetric optical aberrations. These empirical observations appear to agree with subjective patient evaluation and point spread function analysis in evaluating vision improvement. It is preferable to make the diagnostic measurements along the line of sight of the patient's eye and, as before, to perform photoablative treatments with laser beams having fixed or variable diameter spots at the eye target between about 0.5 mm and 7 mm.

In an alternative aspect of this embodiment, a corneal inlay procedure can also be appropriately adjusted based upon the biodynamical and/or biomechanical effects in response to eye trauma. In fact, any refractive procedure will benefit from consideration of biological effects in response to the proposed treatment.

A method according to the invention also applies to reducing regression after photorefractive surgery such as, e.g., PRK or LASIK. In particular, consideration of the biodynamic effect which results in a filling in of high frequency variations in the treated eye surface associated with correction of higher order aberrations can be used to model the eye and adjust a treatment procedure for vision correction.

In a further embodiment according to the invention, a system for performing refractive surgery is improved by including a diagnostic measurement instrument such as, e.g., a wavefront measuring instrument, to the photoablative laser system such that the desired diagnostic measurement on the patient's eye can be made while the patient is in the same position as when the necessary eye trauma is inflicted for the intended surgical procedure. This has a non-limiting benefit of, e.g., removing the effects of eye rotation that occurs when a patient changes from a sitting to a supine position.

The foregoing features, advantages, and objects of the invention are described and illustrated in the detailed description and figures which follow and as set forth in the appended claims.

DETAILED DESCRIPTION OF A PREFERRED EMBODIMENT

The invention relates generally to methods and apparatus for photorefractive treatment to correct or improve vision. In particular, the invention relates to methods and apparatus for developing and carrying out photorefractive treatments related to higher order aberrations in consideration of biodynamical and biomechanical effects on treatment.

Figure 1:
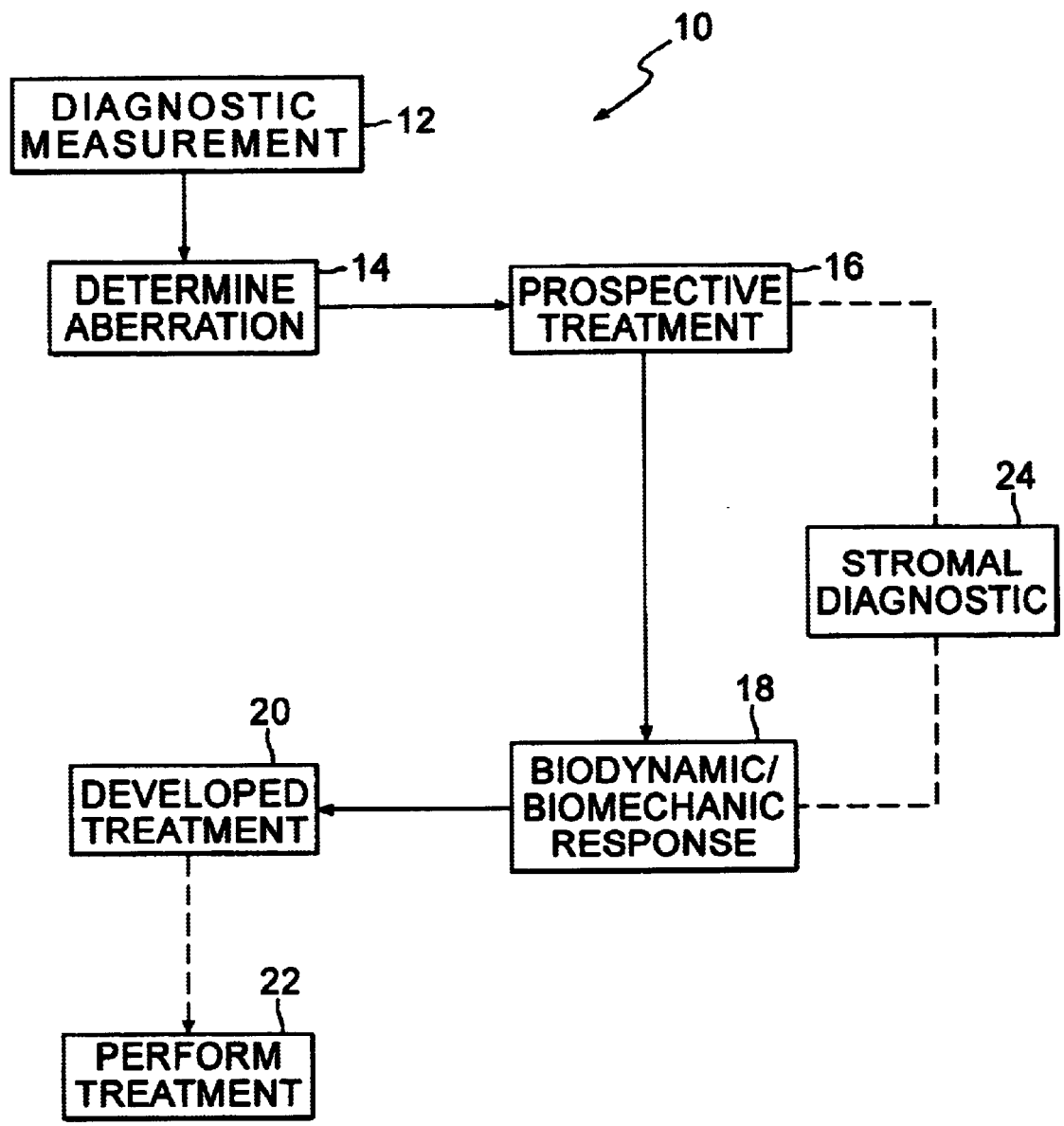
FIG. 1 is a flow chart illustrating the process steps according to an embodiment of the invention.

FIG. 1 shows a series of method steps 10 according to an embodiment of the invention. As illustrated, a diagnostic measurement of a patient's eye is obtained at step 12. This diagnostic measurement 12 is used to determine an optical aberration of the eye in step 14, preferably, but not limited to, a higher order, monochromatic aberration. As that term is used herein, higher order aberration refers to third and higher order Zernike coefficients or their equivalents, while lower order aberrations such as defocus and astigmatism are represented by second and lower order Zernike coefficients or their equivalents. Based generally on past empirical data or other prior information, a prospective treatment 16 is formulated to address the aberrations identified in step 14. The prospective treatment 16, however, is adjusted based upon biodynamical and/or biomechanical effects that are either anticipated, observable, and/or known that would result in the prospective treatment 16 providing less than optimum results in terms of improved vision for the patient. The treatment that is developed in step 20 thus takes into account the biodynamical and/or biomechanical effects that could induce a deviation of the desired result from the prospective treatment. It will be appreciated by those skilled in the art that adjustments to the treatment based upon biodynamical and/or biomechanical effects will tend to be empirically based until enough information is collected to assemble models with more verifiable outcomes. According to aspects of this embodiment, the diagnostic measurement of step 12 can be a direct wavefront measurement such as can be obtained by various wavefront sensors, e.g., ZyWave (Technolas/Bausch & Lomb, Rochester, N.Y.), or by using other diagnostic instruments and techniques such as, for example, topography data from an Orbscan II™ topographer (Orbtek/Bausch & Lomb, Rochester, N.Y.), ultrasound, optical coherence tomography (OCT), pachymetry, and others from which wavefront information can be derived or other useful information can be obtained and which will guide development of a photorefractive treatment. A wavefront measurement is advantageous in that the developed treatment comprises photoablation patterns that may be developed in conjunction with individual aberration orders. The treatment protocol may be single stage or a multi stage treatment such as that described in co-pending application entitled "Method and Apparatus for Multi-Step Correction of Ophthalmic Refractive Errors" filed on Oct. 20, 2000 and incorporated herein by reference in its entirety. That application describes a multi-stage, converging solution approach to photorefractive surgery in which an initial ablation corrects gross defects while a second stage (or subsequent stages) relies, preferably, on a known nomogram for correcting the residual defect.

In an aspect of this embodiment, another diagnostic measurement represented at step 24 can be carried out to further evaluate the biological response of the eye. As illustrated by example in FIG. 1, the stromal/epithelial interface may be measured as well as the stromal profile and/or epithelial thickness which is advantageous because the stroma is the ultimate treated surface in a LASIK procedure, for example. Ultrasonic and OCT techniques are known to obtain these types of measurements.

Performance of the developed treatment is typically carried out using an excimer laser having a wavelength of 193 nm with a fixed or variable beam size of between 0.5 mm to 7 mm in diameter at the target surface. Such lasers are exemplified by the Technolas 217 laser system and the Technolas Zyoptics™ laser vision correction system. Regardless of the device used to perform the developed treatment, based upon empirical data, it has been observed by the inventors that a patient's best vision is obtained when the patient's point spread function is optimized and, or alternatively, the sum total of the residual rotationally symmetric aberrations equals or is greater than the sum total of the residual rotationally asymmetric aberrations, in contrast to hypothetical outcomes of zero wave aberrations.

Figure 2:
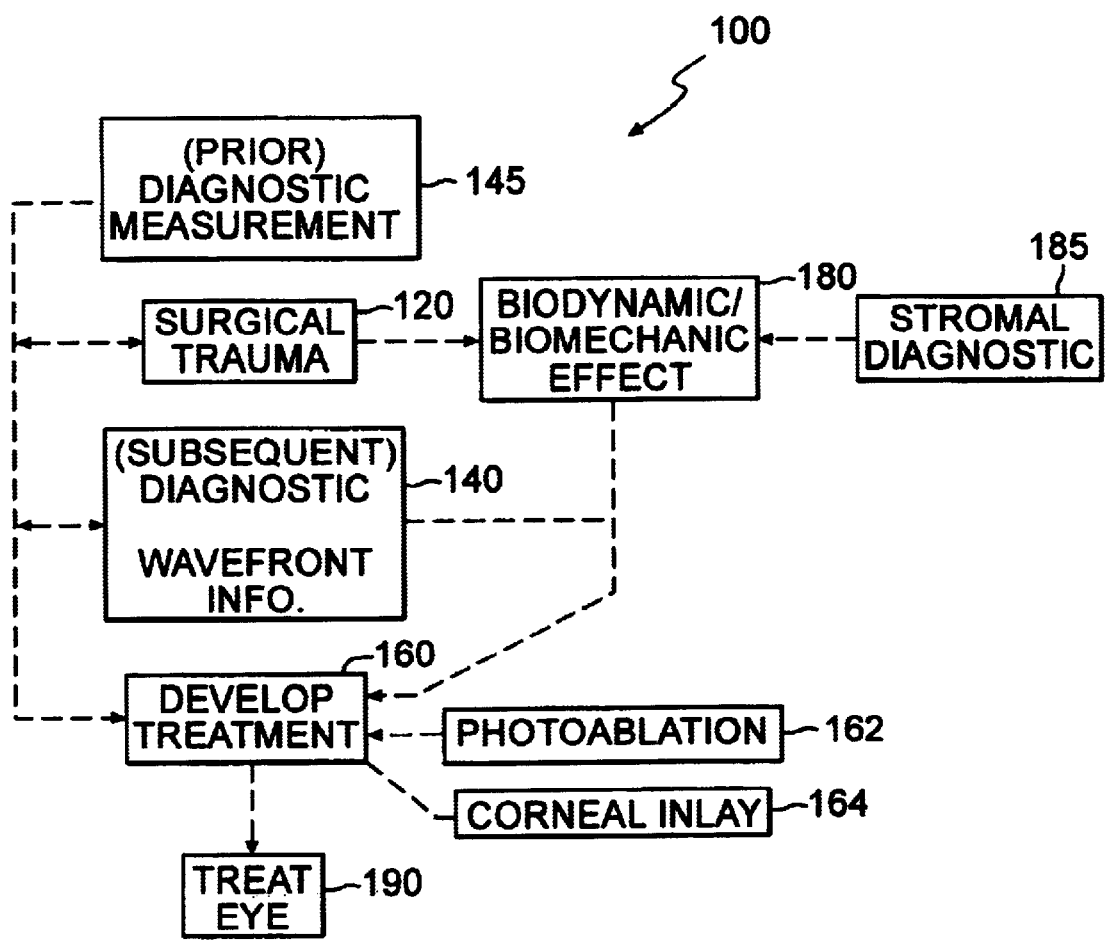
FIG. 2 is a flow chart illustrating the process steps according to an embodiment of the invention.
Figure 3:
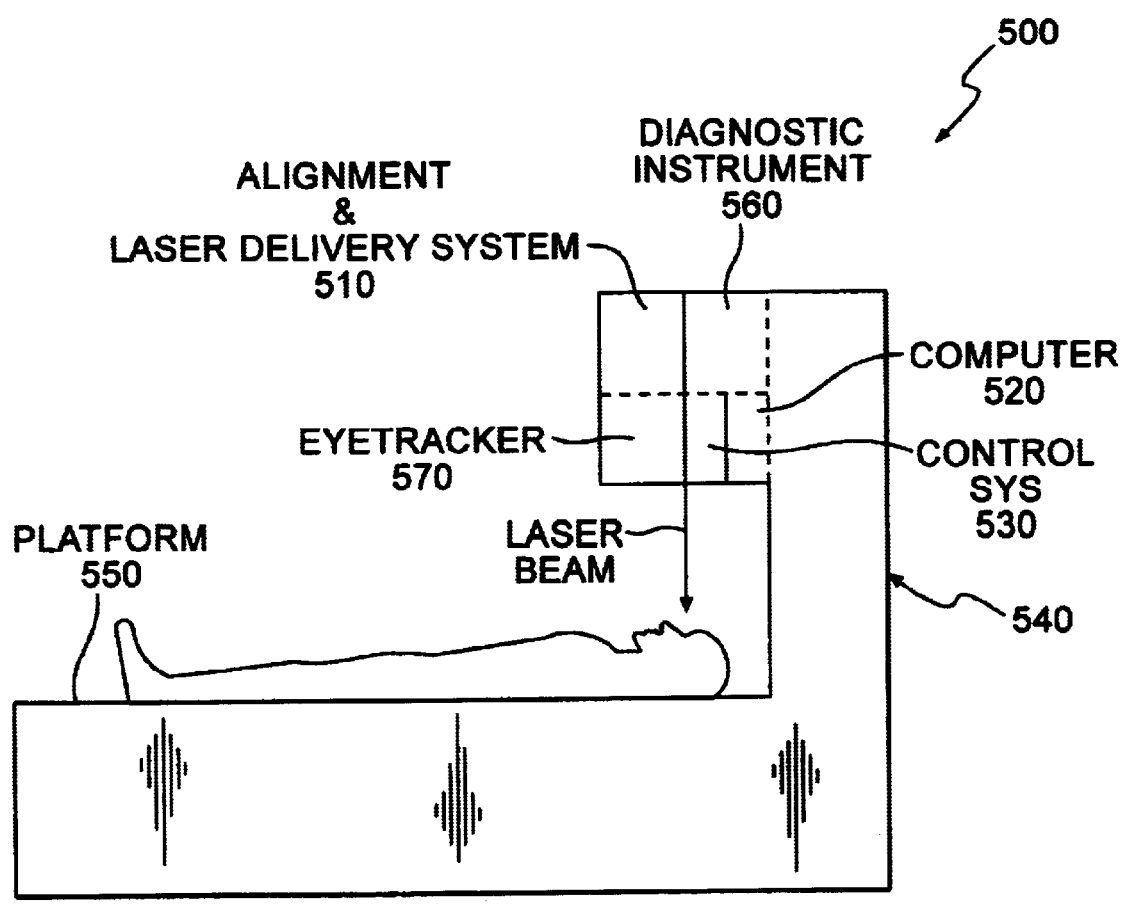
FIG. 3 is a schematic illustration of a photorefractive surgery system according to an embodiment of the invention.

Another embodiment according to the invention is illustrated in connection with the flow diagram shown in FIG. 2. A method for correcting higher order aberrations of a patient's eye 10 includes the basic process steps of inflicting a surgical trauma to the eye 120 corresponding to a particular ophthalmological procedure; i.e., keratectomy or lamellar cut to create a LASIK flap, for example. Other exemplary traumas include corneal scraping, puncture, etc. Diagnostic wavefront information 140 is then obtained subsequent to inflicting the trauma in step 120. A treatment 160 is developed based upon the subsequent diagnostic wavefront information 140. Due to the biological nature of the eye, a biodynamic and/or biomechanical effect 180 is produced in response to the trauma and this biodynamic/biomechanic effect 180 in the form of empirical data, derived data, modeled data, or whatever suitable form the information exists in, can be considered in developing the photorefractive treatment for correcting the higher order aberrations of the patient's eye. In fact, the subsequent diagnostic wavefront information 140 will be indicative to some degree of the biodynamic or biomechanical effect produced in response to the surgical trauma.

An advantageous aspect of this embodiment resides in the optional step of making a prior diagnostic measurement 145 (prior to the surgical trauma) and using the prior diagnostic information in conjunction with the subsequent diagnostic information to develop the photorefractive treatment. For example, the prior diagnostic measurement 145 may provide information about ocular decentration. Such decentration, for example, if unnoticed before the keratectomy, would result in a biodynamic response having different effects than a symmetric keratectomy. When this information is used in connection with directly obtained or derived wavefront information, a prospective treatment can be adjusted based upon biodynamics and/or biomechanics to develop the ultimate treatment 160.

The duration of time between inflicting the surgical trauma and obtaining the subsequent diagnostic wavefront information will be empirically or diagnostically determined by the skilled practitioner. That time suitably will range between immediately after the surgical trauma to as long as one month after the trauma infliction, but preferably sooner rather than later.

Another aspect of this embodiment is illustrated at step 185 wherein an exemplary stromal diagnostic measurement is made to determine the epithelial thickness, stromal profile, or other characteristics which impact or are indicative of a biodynamical effect. This information can then be used in conjunction with the subsequent diagnostic wavefront information 140 and, if obtained, the prior diagnostic measurement information 145 to adjust a prospective treatment profile in order to develop the ultimate treatment 160. Finally, the treatment is carried out at step 190. As referenced above, empirical data suggests that most patients are happier about their corrected vision when a residual sum total of rotationally symmetric aberrations equals or exceeds a residual sum total of rotationally asymmetric aberrations, as opposed to zero residual aberrations or some other combination of residual higher order aberrations.

Although the method embodiment described above relates generally to a photoablative treatment of the eye, it will be appreciated by those skilled in the art that the method also lends itself to a corneal inlay procedure. In fact, any surgical vision correction or vision improvement procedure would benefit from consideration of biodynamic and biomechanical effects produced in response to any aspect of the surgical treatment.

Another embodiment according to the invention describes a method for lessening regression that often results after photorefractive treatment of a patient's eye. The method basically consists of adjusting a prospective treatment for modifying an optical aberration of the patient's eye in consideration of at least a biodynamic or a biomechanical effect of the eye in response to any portion of the prospective treatment. Such biodynamic effects include, but are not limited to, epithelial growth, edema, and other biological responses, while the biomechanical effects are understood to include but not be limited to the effect of eyelid pressure on stromal smoothing. For example, it is postulated that when higher order aberrations are addressed by photoablation, a high frequency variation in the treated stromal surface results. However, over time these high frequency variations are filled in by epithelial cells that are constantly pushed and scrapped by the pressure of the eyelid during the blinking response. Ultimately, empirical data suggests that whatever adjustments are made, the residual sum total of the rotationally symmetric aberrations should equal or exceed the residual sum total of the rotationally asymmetric aberrations.

FIG. 5 shows a system embodiment 500 according to the invention. The system 500 is an improved system for refractive surgery on a patient's eye. Conventional systems include a laser system 510 suitable for photorefractive correction of eye tissue. A computer 520 is typically linked to the laser system 510 and is used, at least in part, to develop the photorefractive treatment. A laser control system 530 is linked to the laser system and the computer to control the firing of the laser. A viewing system 540, typically in the form of a microscope and/or display screen, for example, is further linked to the laser system for visualization of the patient's eye during treatment by the practitioner. A suitable platform 550 is provided to situate the patient in the surgical position, typically a supine position. Additionally, many of the refractive surgery systems include an eyetracker 570. The computer 520, control system 530, viewing system 540, and platform 550 may be separated from or integrated with the refractive surgery system. The improvement according to the invention includes a diagnostic measuring instrument 560 that is linked to the system in such a manner that the patient need not change their position from the surgical position in order to obtain the diagnostic information. For example, a wavefront sensor, a topography unit, an ultrasound unit, a pachymetry device, a OCT device or other suitable diagnostic instrument or any combination thereof, could be positioned in the refractive surgery system overhead of the patient and aligned to the patient's line of sight to coincide with the photorefractive treatment alignment. Alignment techniques and systems for the laser system and one or more diagnostic instruments are described in co-pending patent application entitled "Customized Corneal Profiling" filed on Oct. 20, 2000 and incorporated herein by reference in its entirety.

While various advantageous embodiments have been chosen to illustrate the invention, it will be understood by those skilled in the art that various changes and modifications can be made therein without departing from the scope of the invention as defined in the appended claims.

We claim:

1. A method for correcting for higher order aberrations of a patient's eye, comprising:

inflicting a required surgical trauma to the eye corresponding to a particular ophthamological procedure;

obtaining diagnostic wavefront information subsequent to inflicting the trauma;

developing a treatment for correcting the higher order aberrations of the patient's eye based at least in part upon the subsequent wavefront information.

2. The method of claim 1, wherein the surgical trauma includes at least one of a lamellar corneal cut, a keratectomy, a keratotomy, a corneal abrasion, a corneal puncture, a corneal incision.

3. The method of claim 2, wherein said trauma is a keratome cut to create a LASIK flap and further wherein said diagnostic wavefront information is obtained prior to lifting said flap.

4. The method of claim 1, wherein developing the treatment comprises considering a biodynamical effect in response to the trauma, further wherein said subsequent wavefront information includes indicia of said biodynamical effect.

5. The method of claim 4, wherein developing the treatment includes determining an ablation profile that is adjusted with respect to a prospective ablation profile associated with correcting the higher order aberrations in the absence of considering the biodynamical effect in response to the trauma.

6. The method of claim 5, wherein said adjustment is an empirical based adjustment.

7. The method of claim 1, further comprising obtaining a diagnostic measurement of the patient's eye prior to inflicting the surgical trauma.

8. The method of claim 7, further comprising using said prior diagnostic information and said subsequent wavefront information to develop said treatment.

9. The method of claim 1, wherein said subsequent wavefront information is obtained at a time after the infliction of the surgical trauma ranging from substantially immediately to an empirically or diagnostically determined time in consideration of a biodynamic effect of the eye in response to the surgical trauma.

10. The method of claim 9, wherein said determined time is within one month of said trauma infliction.

11. The method of claim 1, wherein said obtained wavefront information is at least one of a direct wavefront measurement or derived from a non-direct wavefront measurement.

12. The method of claim 1, further comprising:

considering a prospective biomechanical effect of the eye with respect to the developed treatment; and adjusting said developed treatment, at least in part, as a function of the prospective biomechanical effect of the eye.

13. The method of claim 1, further comprising obtaining a different diagnostic measurement indicative of a characteristic of the epithelium of the eye, and using information from this measurement to adjust the developed treatment to compensate for a biomechanical effect of the eye.

14. The method of claim 13, wherein said epithelium characteristic includes at least one of an epithelial profile and epithelial thickness.

15. The method of claim 1, further comprising treating the eye.

16. The method of claim 15, wherein after said treatment, the sum total of rotationally symmetric aberrations is equal to or greater than a sum total of rotationally asymmetric aberrations.

17. The method of claim 15, comprising performing a photoablative treatment with a laser beam having a diameter, d, at a target location between $0.5 \text{ mm} \leq d \leq 7 \text{ mm}$.

18. The method of claim 15, wherein said treatment includes at least one of photo-ablation and a corneal inlay.

19. The method of claim 18, comprising performing a photoablative treatment with a laser beam having a diameter, d, at a target location between $0.5 \text{ mm} \leq d \leq 7 \text{ mm}$.

20. The method of claim 1, wherein said diagnostic wavefront information is obtained by a measurement made through a line of sight of the patient's eye.

* * * * *